(12) United States Patent
Numata (10) Patent No.: US 10,194,084 B2
(45) Date of Patent: Jan. 29, 2019

(54) IMAGE PROCESSING DEVICE AND COMPUTER-READABLE STORAGE DEVICE FOR SELECTIVELY OUTPUTTING REFERENCE IMAGE AND SYNTHESIZED IMAGE

(71) Applicant: OLYMPUS CORPORATION, Tokyo (JP)

(72) Inventor: Kenji Numata, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/686,450

(22) Filed: Aug. 25, 2017

(65) Prior Publication Data

US 2017/0353666 A1    Dec. 7, 2017

Related U.S. Application Data

(63) Continuation of application No. PCT/JP2016/081303, filed on Oct. 21, 2016.

(30) Foreign Application Priority Data

Nov. 18, 2015    (JP) .................................. 2015-226011

(51) Int. Cl.
*H04N 5/228*    (2006.01)
*H04N 5/222*    (2006.01)
(Continued)

(52) U.S. Cl.
CPC ........... *H04N 5/23267* (2013.01); *A61B 1/04* (2013.01); *G06T 5/002* (2013.01); *G06T 5/003* (2013.01);
(Continued)

(58) Field of Classification Search
CPC .......... H04N 5/23254; H04N 5/23229; H04N 5/23293; G06T 7/20; G06T 7/207;
(Continued)

(56) References Cited

U.S. PATENT DOCUMENTS 5,270,810 A    12/1993    Nishimura
7,826,730 B2 *    11/2010    Wakamatsu ........... G03B 17/00
                                                348/208.4
(Continued)

FOREIGN PATENT DOCUMENTS

JP    H04-259442 A    9/1992
JP    2010-155031 A    7/2010
JP    2015-041924 A    3/2015

OTHER PUBLICATIONS

International Search Report dated Dec. 13, 2016 issued in PCT/JP2016/081303.

*Primary Examiner* — Ngoc Yen T Vu
(74) *Attorney, Agent, or Firm* — Scully, Scott, Murphy & Presser, P.C.

(57) ABSTRACT

An image processing device including: one or more processors comprising hardware, wherein the one or more processors are configured to: calculate an estimated movement amount of a subject in each image of a plurality of images; perform, based on the estimated movement amounts, one of: select and output an image that is most recently captured among the plurality of images; and select a reference image from the plurality of images based on the estimated movement amounts of the subject in the plurality of images; in response to selecting the reference image, determine a gain of the reference image; and perform, based on the gain, one of: select and output the reference image; and a synthesis process including: select a synthesis target image from the (Continued)

plurality of images; and generate and output a synthesized image by synthesizing the synthesis target image and the reference image.

12 Claims, 7 Drawing Sheets

(51) Int. Cl.
| | |
|---|---|
| *H04N 5/232* | (2006.01) |
| *A61B 1/04* | (2006.01) |
| *G06T 7/20* | (2017.01) |
| *G06T 7/246* | (2017.01) |
| *G06T 5/00* | (2006.01) |
| *H04N 5/272* | (2006.01) |
| *H04N 7/01* | (2006.01) |
| *H04N 7/18* | (2006.01) |
| *G06T 3/00* | (2006.01) |
| *H04N 5/225* | (2006.01) |

(52) U.S. Cl.
CPC ............... *G06T 7/20* (2013.01); *G06T 7/248* (2017.01); *H04N 5/23229* (2013.01); *H04N 5/23254* (2013.01); *H04N 5/23293* (2013.01); *H04N 5/272* (2013.01); *H04N 7/012* (2013.01); *G06T 3/0068* (2013.01); *G06T 2207/10068* (2013.01); *G06T 2207/20004* (2013.01); *H04N 5/2256* (2013.01); *H04N 2005/2255* (2013.01)

(58) Field of Classification Search
CPC ................... G06T 7/215; G06T 7/248; G06T 2207/20004; G06T 5/003
See application file for complete search history.

(56) References Cited

U.S. PATENT DOCUMENTS

| | | | |
|---|---|---|---|
| 7,990,428 B2 * | 8/2011 | Yano | .................... H04N 5/2625 348/208.13 |
| 9,299,147 B2 * | 3/2016 | Shimizu | ................ G06T 7/0028 |
| 2012/0019686 A1 * | 1/2012 | Manabe | .................. G06T 5/009 348/222.1 |
| 2016/0180508 A1 | 6/2016 | Hamada | |

* cited by examiner

IMAGE PROCESSING DEVICE AND COMPUTER-READABLE STORAGE DEVICE FOR SELECTIVELY OUTPUTTING REFERENCE IMAGE AND SYNTHESIZED IMAGE

CROSS-REFERENCE TO RELATED APPLICATIONS

This application is a continuation application of PCT International Application No. PCT/JP2016/081303, filed on Oct. 21, 2016, claiming priority based on Japanese Patent Application No. JP 2015-226011, filed on Oct. 21, 2016, the content of each of which is incorporated herein by reference.

BACKGROUND

Technical Field

The present invention relates to an image processing device, an image processing method, and a program. The present application claims priority rights based on Japanese Patent Application No. 2015-226011 filed on Nov. 18, 2015, and the contents of which are hereby incorporated by reference.

Description of Related Art

An endoscope device displays both fields (an ODD field and an EVEN field) of an imaging signal of an interlacing type so as to increase a sense of resolution. In this way, in a state where a front end of an insertion portion of the endoscope device swings in a case where both fields are displayed, there is a possibility that an image blurs between the ODD field and the EVEN field and this causes interlaced noise.

Hence, a method is known in which, at the time of freezing (capturing a still image), an image with the smallest blurring is selected from among each frame accumulated for a predetermined period (for example, for approximately one second), furthermore, noise reduction processing (hereinafter, referred to as NR processing on a plurality of frames) is performed by using information of a plurality of frames in the vicinity of the selected image, and thereby, a freeze image (still image) avoiding the interlaced noise is generated (refer to, for example, PTL 1).

CITATION LIST

Patent Literature

PTL 1: JP-A-2015-41924

For example, the technique described in PTL 1 has a possibility that, in a case where the front end of an insertion portion of an endoscope device constantly swings for a predetermined period in which frames are accumulated, even a frame with the smallest blurring eventually blurs, and a freeze image which does not obtain NR effects is displayed even if NR processing on a plurality of frames is performed.

SUMMARY

In view of the above circumstances, some aspects of the present invention are to provide an image processing device, an image processing method, and a computer-readable storage device which can generate a freeze image with better image quality.

An aspect of the present invention is an image processing device comprising: one or more processors comprising hardware, wherein the one or more processors are configured to: calculate an estimated movement amount of a subject in each image of a plurality of images; perform, based on the estimated movement amounts of the plurality of images, one of: select and output an image that is most recently captured among the plurality of images; and select a reference image from the plurality of images based on the estimated movement amounts of the subject in the plurality of images; in response to selecting the reference image, determine a gain of the reference image; and perform, based on the gain of the reference image, one of: select and output the reference image; and a synthesis process comprising: select a synthesis target image from the plurality of images, the synthesis target image being different from the reference image; and generate and output a synthesized image by synthesizing the synthesis target image and the reference image.

Another aspect of the present invention is a method comprising: calculating an estimated movement amount of a subject in each image of a plurality of images; performing, based on the estimated movement amounts of the plurality of images, one of: selecting and outputting an image that is most recently captured among the plurality of images; and selecting a reference image from the plurality of images based on the estimated movement amounts of the subject in the plurality of images; in response to selecting the reference image, determining a gain of the reference image; and performing, based on the gain of the reference image, one of: selecting and outputting the reference image; and a synthesis process comprising: selecting a synthesis target image from the plurality of images, the synthesis target image being different from the reference image; and generating and outputting a synthesized image by synthesizing the synthesis target image and the reference image.

Still another aspect of the present invention is a computer-readable storage device storing instructions that cause a computer to at least: calculate an estimated movement amount of a subject in each image of a plurality of images; perform, based on the estimated movement amounts of the plurality of images, one of: select and output an image that is most recently captured among the plurality of images; and select a reference image from the plurality of images based on the estimated movement amounts of the subject in the plurality of images; in response to selecting the reference image, determine a gain of the reference image; and perform, based on the gain of the reference image, one of: select and output the reference image; and a synthesis process comprising: select a synthesis target image from the plurality of images, the synthesis target image being different from the reference image; and generate and output a synthesized image by synthesizing the synthesis target image and the reference image.

DETAILED DESCRIPTION

Figure 1:
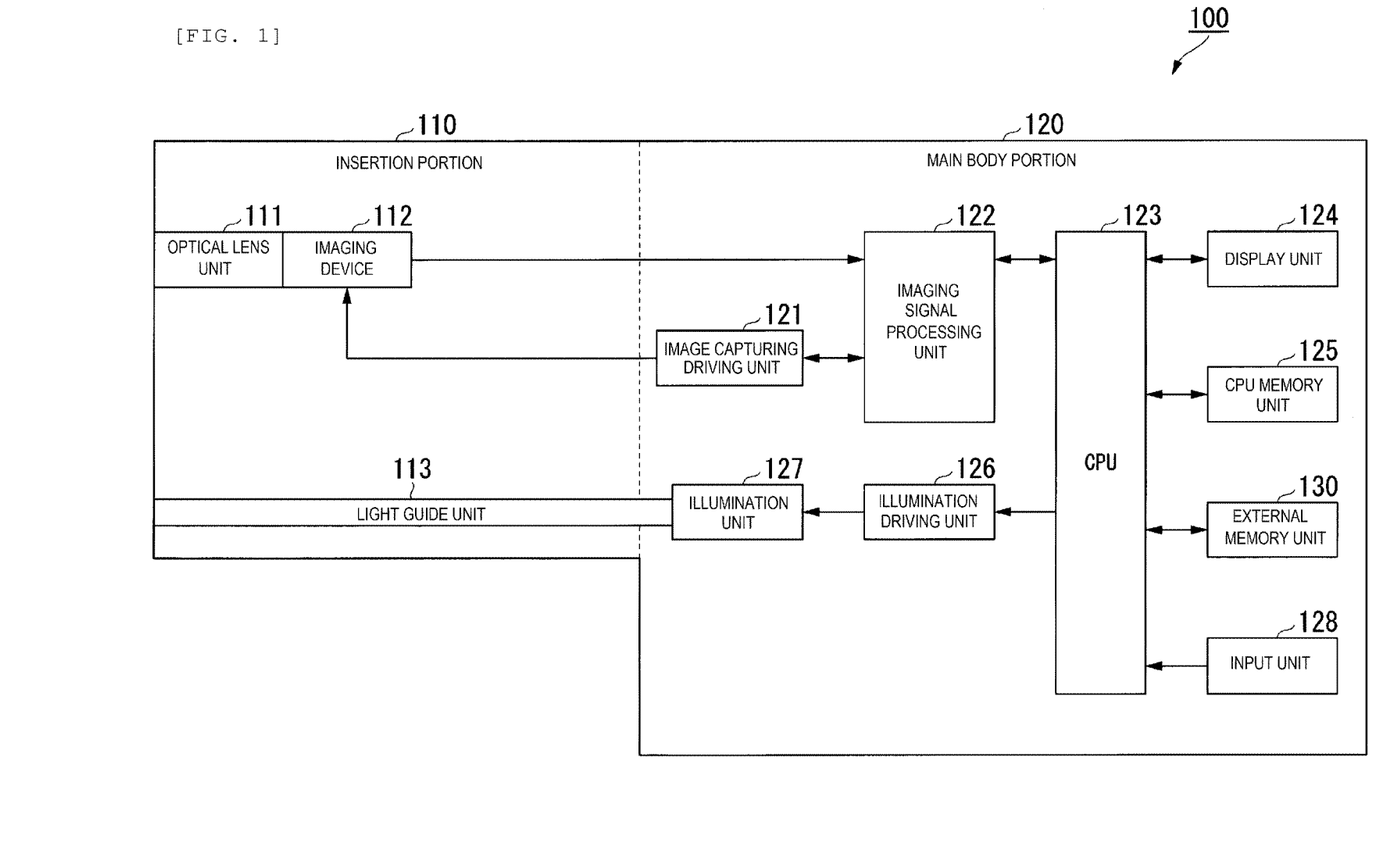
FIG. 1 is a block diagram illustrating a configuration of an endoscope device according to an embodiment of the present invention.

Hereinafter, one embodiment of the present invention will be described below with reference to the drawings. FIG. 1 is a block diagram illustrating a configuration of an endoscope device according to the present embodiment. In the illustrated example, the endoscope device 100 includes a thin and long insertion portion 110 and a main body portion 120. In addition, an external memory unit 130 (for example, a recording medium) can be attached to the main body portion 120, and a still image, a moving image, and the like which are captured by the endoscope device 100 can be recorded in the external memory unit 130.

The insertion portion 110 has a tubular shape with a diameter of approximately 4 to 6 mm. The insertion portion 110 includes an optical lens unit 111, an imaging device (CCD (Charge Coupled Device)) 112, and a light guide unit 113. The main body portion 120 includes an image capturing driving unit 121, an imaging signal processing unit 122, a CPU (Central Processing Unit) 123 (control unit), a display unit 124, a CPU memory unit 125, an illumination driving unit 126, an illumination unit 127, and an input unit 128.

The input unit 128 includes a switch, a joystick for bending a front end of an endoscope or the like, receives an input of an instruction from a user, and outputs a signal based on the received input to the CPU 123. The instruction from the user includes, for example, an instruction of zoom magnification, an instruction of brightness of an image to be captured, an instruction to light or extinguish the illumination unit 127, an instruction to bend the insertion portion 110, an instruction to record an image to the external memory unit 130, an instruction to display an image on the display unit 124, and the like.

The CPU 123 controls each unit included in the endoscope device 100 so as to perform processing based on a signal input from the input unit 128. For example, in a case where the input unit 128 receives an input to instruct a zoom magnification and an input to instruct brightness of an image to be captured, the CPU 123 controls the imaging signal processing unit 122 such that the processing based on the input received by the input unit 128 is performed. In addition, in a case where the input unit 128 receives an input for instructing to light or extinguish the illumination unit 127, the CPU 123 controls the illumination driving unit 126 such that processing based on the input received by the input unit 128 is performed.

In a case where the input unit 128 receives an input to instruct bending of the insertion portion 110, the CPU 123 controls bending control means (not illustrated) such that processing based on the input received by the input unit 128 is performed. In a case where the input unit 128 receives an input to instruct recording of an image in the external memory unit 130, the CPU 123 performs processing of recording the image in the external memory unit 130. In a case where the input unit 128 receives an input to instruct display of an image in the display unit 124, the CPU 123 performs processing of displaying an image in the display unit 124. The display unit 124 is, for example, an LCD (Liquid Crystal Display), and displays an image.

The CPU memory unit 125 is, for example, a RAM (Random Access Memory), a ROM (Read Only Memory) or the like, and stores an operation program of the CPU 123. In addition, the CPU memory unit 125 stores data used for processing of the CPU 123.

The illumination unit 127 is, for example, an LED (Light Emitting Diode), and emits light. The illumination unit 127 is connected to the illumination driving unit 126. The illumination driving unit 126 is connected to the CPU 123. The illumination driving unit 126 controls lighting and extinguishing of the illumination unit 127 on the basis of an illumination lighting signal which is input from the CPU 123. The illumination unit 127 is lighted or extinguished under control of the illumination driving unit 126. The light guide unit 113 guides light emitted by the illumination unit 127 to a front end of the insertion portion 110. Thereby, the endoscope device 100 can irradiate, for example, a subject with light.

The optical lens unit 111 forms an image of the subject illuminated by the illumination unit 127 and the light guide unit 113 on a light receiving surface of the imaging device 112. The imaging device 112 is connected to the image capturing driving unit 121 by, for example, a composite coaxial cable. The image capturing driving unit 121 receives a timing signal for driving the imaging device 112 from a timing generator provided in the imaging signal processing unit 122. The image capturing driving unit 121 performs drive processing of the received timing signal, according to a transmission path length to the imaging device 112 (length of the composite coaxial cable), and transmits the processed timing signal to the imaging device 112 as an imaging device drive signal.

The imaging device 112 performs a photoelectric conversion of the light formed on the light receiving surface, based on timing of the transmitted imaging device drive signal, and outputs the photoelectrically converted signal as an imaging device output signal. The imaging device output signal output by the imaging device 112 is input to the imaging signal processing unit 122 via the composite coaxial cable.

The imaging signal processing unit 122 generates an image by using the imaging device output signal which is input, based on control of the CPU 123. For example, the imaging signal processing unit 122 performs various camera signal processing, such as demosaicing, gamma correction, NR processing on a plurality of frames which will be described below, white balance correction, contour correction, electronic zoom processing, color correction, contrast correction, AE control, and the like. In addition, the imaging signal processing unit 122 outputs the generated image (frame) to the CPU 123 as image data. The imaging signal processing unit 122 selects a freeze image or an image used as a measurement image.

The CPU 123 performs image processing (color space conversion, motion adaptive interlace/progressive conversion (hereinafter, referred to as motion adaptive I/P conversion), 2D and 3D NR, scaling processing of contraction/expansion processing, OSD display overlapping processing of menu or the like, encoding/decoding processing of a still image format or a moving image format, freeze processing, and the like) of on the image data which is input.

The CPU 123 displays the image data whose image processing is completed in, for example, the display unit 124. In addition, the CPU 123 stores the image data which is input in, for example, the external memory unit 130. For example, in a case where recording an image is performed after freeze processing (acquisition processing of a still image) is performed, the CPU 123 stores the still image in the external memory unit 130. In addition, for example, in a case where recording an image is performed without performing the freeze processing, the CPU 123 stores the moving image in the external memory unit 130.

Figure 2:
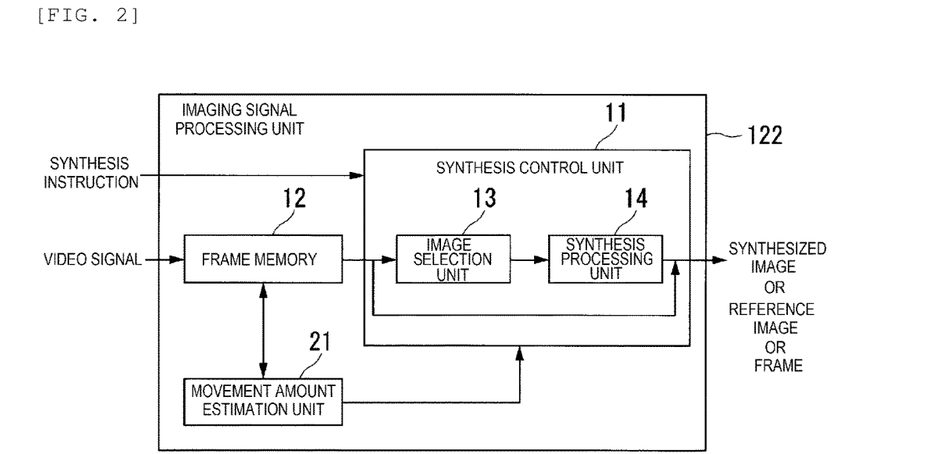
FIG. 2 is a block diagram illustrating a configuration of an imaging signal processing unit according to the present embodiment.

Next, the imaging signal processing unit 122 will be described in detail. FIG. 2 is a block diagram illustrating a configuration of the imaging signal processing unit 122. In the illustrated example, the imaging signal processing unit 122 includes a synthesis control unit 11, a frame memory 12 (memory), and a movement amount estimation unit 21. The synthesis control unit 11 includes an image selection unit 13 and a synthesis processing unit 14, and generates a synthesized image by using frames stored in the frame memory 12. In addition, the synthesis control unit 11 can also output a reference image selected by the image selection unit 13 and the frame stored in the frame memory 12. The frame memory 12 stores the video signal which is input. The video signal is, for example, a moving image, and includes frames which are consecutively captured.

The movement amount estimation unit 21 estimates a movement amount X (estimated movement amount) of a subject. The movement amount X and a method of estimating the movement amount X will be described below. If a synthesis instruction is input, the image selection unit 13 selects a reference image which is a reference of synthesis from the frames included in the video signal stored in the frame memory 12, based on the movement amount X. In addition, the image selection unit 13 selects a plurality of synthesis target images which are synthesized with the selected reference image. Details of a reference image selecting method and a synthesis target image selecting method will be described below. The synthesis processing unit 14 synthesizes the synthesis target image with the reference image selected by the image selection unit 13, and generates a synthesized image. The synthesized image generated by the synthesis processing unit 14 is an image from which noise in a temporal direction of the reference image is removed. That is, the synthesis processing unit 14 performs noise removal processing of the reference image by synthesizing the synthesis target image with the reference image.

Figure 3:
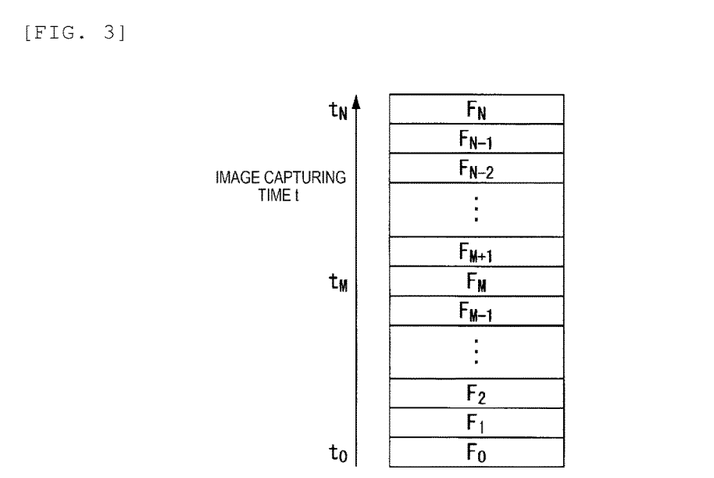
FIG. 3 is a schematic diagram illustrating an example of a frame stored in a frame memory according to the present embodiment.

Next, an example of the frame stored in the frame memory will be described. FIG. 3 is a schematic diagram illustrating an example of the frame stored in the frame memory 12 in the present embodiment. In the illustrated example, the frame memory 12 stores N frames $F_0$, $F_1$, $F_2$, ..., $F_{M-1}$, $F_M$, $F_{M+1}$, $F_{N-2}$, $F_{N-1}$, $F_N$ which have different image capturing times t (N is a natural number, M is an integer of 0 to N). In addition, in the example illustrated in the figure, images are sequentially captured from the frame $F_0$ to the frame $F_N$, image capturing time of the frame $F_0$ is the oldest, and image capturing time of the frame $F_N$ is the newest. For example, the image capturing time of the frame $F_0$ is $t_0$ and the image capturing time of the frame $F_1$ is $t_1$. In the same manner, the image capturing times of the other frames $F_2$ to $F_N$ are $t_2$ to $t_N$. In a case where the frames stored in the frame memory 12 are N pieces, and in a case where a new frame is input to the frame memory 12, the oldest frame is deleted and a new frame is stored.

Figure 4:
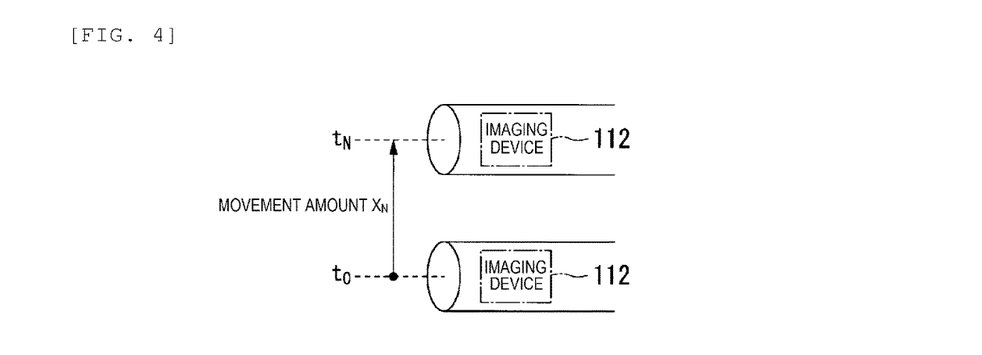
FIG. 4 is a schematic diagram illustrating a relationship between timing when an imaging device captures an image and a position of the imaging device in the present embodiment.

Next, the video signal which is input to the frame memory 12 will be described. For example, the video signal which is input to the frame memory 12 is a video signal captured by the imaging device 112 included in the endoscope device 100. FIG. 4 is a schematic diagram illustrating a relationship between timing when the imaging device 112 provided in the endoscope device captures an image and a position of the imaging device 112. In the illustrated example, the imaging device 112 captures an image of the subject during a period from time $t_0$ to time $t_N$. The imaging device 112 outputs the frame $F_0$ at the time $t_0$, and outputs the frame $F_N$ at the time $T_N$ (see FIG. 3). In addition, positions of the imaging devices 112 are different at the time $t_0$ and the time $t_N$. The amount of changes at the position of the imaging device 112 is referred to as the movement amount X. In the illustrated example, the movement amount X between the imaging device 112 at the time t0 and the imaging device 112 at the time $t_N$ is $X_N$.

Hence, in a case where the subject is stationary, the imaging device 112 is moving, and thus, the position of the subject in the frame $F_0$ is different from the position of the subject in the frame $F_N$. Hence, in a case where the frame $F_0$ and the frame $F_N$ are synthesized to generate a synthesized image, it is necessary to perform synthesis processing after alignment is performed such that the position of the subject of the frame $F_0$ and the position of the subject of the frame $F_N$ are at the same position.

Figure 5:
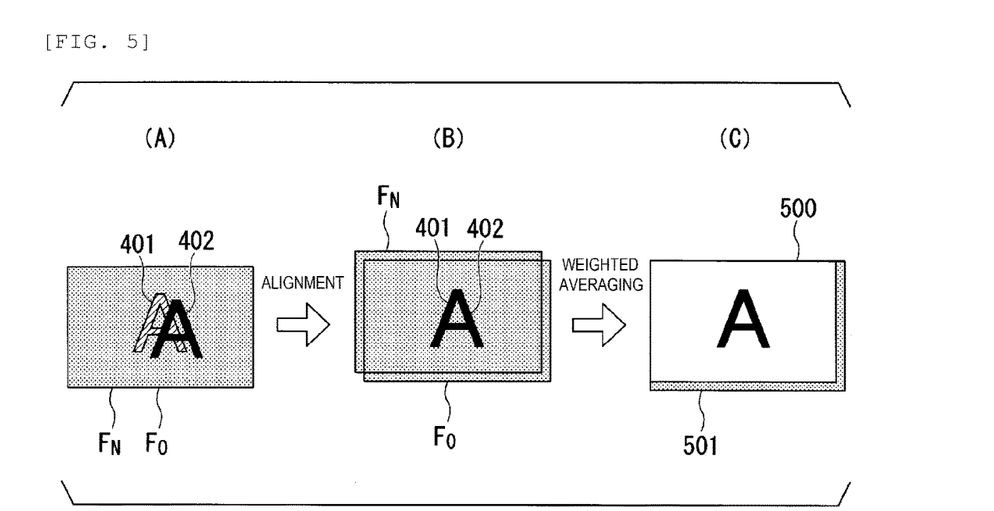
FIG. 5 is a schematic diagram illustrating a processing sequence for synthesizing a frame $F_O$ and a frame $F_N$ and generating a synthesized image.

FIG. 5 is a schematic diagram illustrating a processing sequence when the frame $F_0$ and the frame $F_N$ are synthesized to generate a synthesized image. In the example illustrated in the figure, the frame $F_0$ output from the imaging device 112 illustrated in FIG. 4 is used as a reference image and the frame $F_N$ is used as the synthesis target image (see FIG. 3 for the frame). In addition, an image of a character "A" is captured as a subject. In addition, both the frame $F_0$ and the frame $F_N$ include noise.

Part A of FIG. 5 is a schematic diagram illustrating an image obtained by overlapping the frame $F_0$ and the frame $F_N$. Positions of the imaging device 112 differ from each other at the time $t_0$ when the frame $F_0$ is captured and at the time $t_N$ when the frame $F_N$ is captured. For this reason, in the illustrated example, a position of the subject "A" 401 in the frame $F_0$ differs from a position of the subject "A" 402 in the frame $F_N$ by movement amount $X_N$. The amount by which the subject "A" in the synthesis target image (frame $F_N$) is shifted from the subject "A" in the reference image (frame $F_0$) is referred to as a blurring amount.

Part B of FIG. 5 is a schematic diagram illustrating mutual frames in a state where the position of the subject "A" of the frame $F_0$ and the position of the subject "A" of the frame $F_N$ are aligned. In the illustrated example, since the frame $F_0$ is the reference image, the synthesis processing unit 14 performs processing of aligning the position of the subject "A" 402 in the frame $F_N$ which is the synthesis target image with the position of the subject "A" 401 in the frame $F_0$. In this way, in order to move the position of the frame $F_N$, in a case where a position of the subject is aligned, a region where the frame $F_0$ overlaps the frame $F_N$, and a region where the frame $F_0$ does not overlap the frame $F_N$ are generated.

Part C of FIG. 5 is a schematic diagram illustrating a synthesized image 500 generated by performing weighted averaging of the frame $F_0$ and the frame $F_N$ which are aligned. The region of the synthesized image 500 is the same as the region of the frame $F_0$ which is the reference image. In the illustrated example, noise in the region where the frame $F_0$ overlaps the frame $F_N$ is reduced. However, since the synthesized image 500 is generated by performing the weighted averaging of the frame $F_0$ and the frame $F_N$, luminance of a region 501 where the frame $F_0$ does not overlap the frame $F_N$ is dark.

Hence, a maximum blurring amount of the synthesis target image which is allowable is determined in accordance with an allowable range of the region 501. That is, the maximum blurring amount is defined for the synthesis target image which is used for generating the synthesized image 500. For example, in a case where the allowable range of the region 501 is wide, it is possible to use a synthesis target image having a large blurring amount when the synthesized image 500 is generated. In addition, in a case where the allowable range of the region 501 is narrow, it is not possible to use the synthesis target image having a large blurring amount when the synthesized image 500 is generated. If the movement amount X of the imaging device 112 increases, the blurring amount of the synthesis target image increases. Hence, the allowable movement amount X of the imaging device 112 is determined in accordance with the allowable range of the region 501.

Next, a method of estimating the movement amount X of the subject by using the movement amount estimation unit 21 will be described. There are several methods of estimating the movement amount X of the subject, but any method may be used as long as the method can estimate the movement amount. For example, there are a method of estimating the movement amount of the subject in a newly input frame by comparing luminance values of the newly input frame with a frame which is input prior to the previous frame, and a method of detecting the movement amount X of the imaging device 112 by using a sensor and considering the detected movement amount of the imaging device 112 as the movement amount X of the subject in an environment where there is almost no motion of the subject itself. Although it is described as frame processing here, in a case where the processing is performed by interlacing, the movement amount X of the subject may be estimated by using an interlaced image which is newly input and an interlaced image which is input prior to the previous image.

Next, a processing sequence in which the endoscope device 100 starts image capturing to generate a freeze image (still image) will be described. In the present embodiment, the imaging signal processing unit 122 and the CPU 123 respectively perform processing to generate the freeze image.

Figure 6:
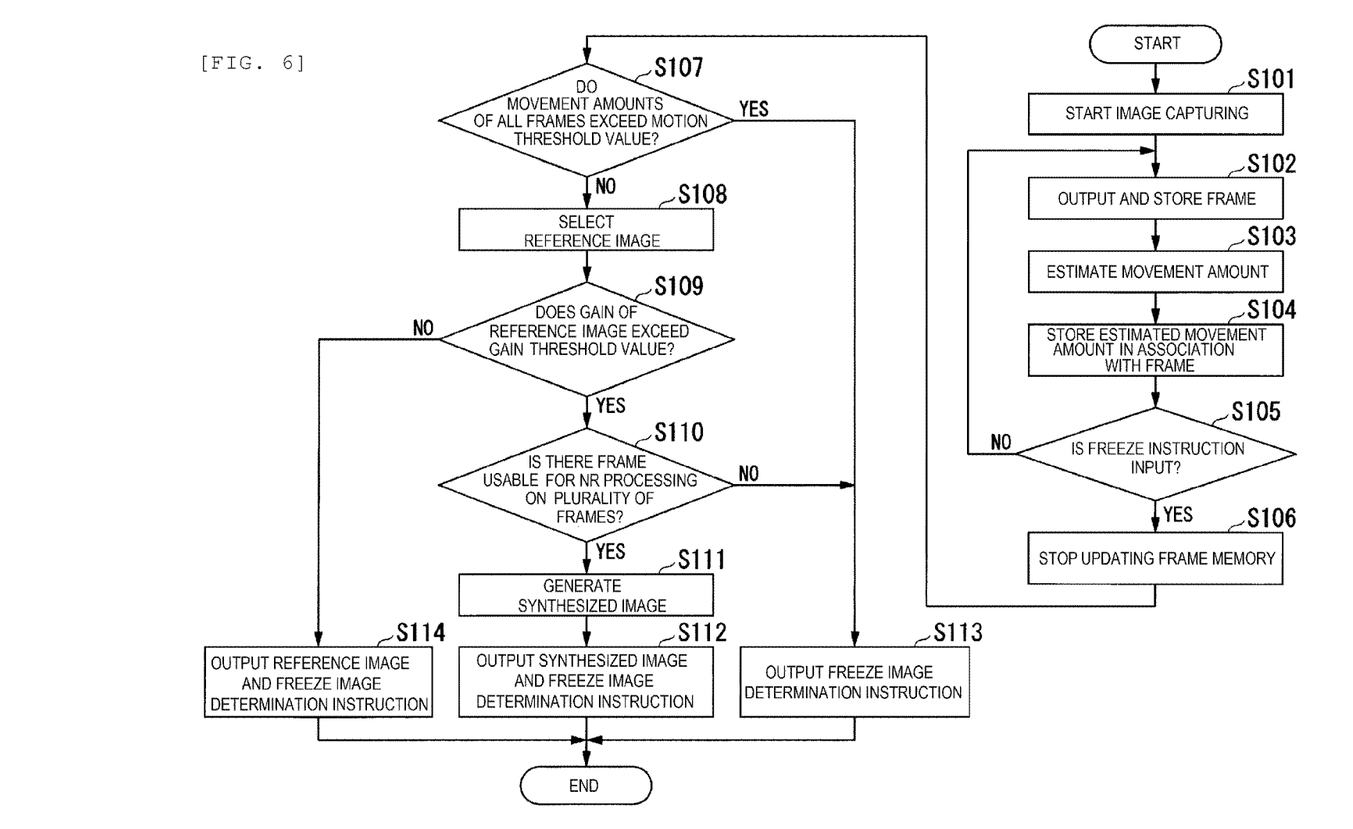
FIG. 6 is a flowchart illustrating an operation sequence of the imaging signal processing unit when the endoscope device starts image capturing to generate a freeze image in the present embodiment.

FIG. 6 is a flowchart illustrating an operation sequence of the imaging signal processing unit 122 when the endoscope device 100 starts image capturing to generate a freeze image in the present embodiment.

(step S101) In a case where the endoscope device 100 starts image capturing, the imaging signal processing unit 122 controls the image capturing driving unit 121 to make the imaging device 112 start image capturing. Thereafter, the processing proceeds to step S102.

(step S102) The imaging signal processing unit 122 outputs frames (video signal) which are input from the outside one by one to the CPU 123. In addition, the imaging signal processing unit 122 stores the frames (video signal) which is input from the outside one by one in the frame memory 12. In a case where the frames stored in the frame memory 12 is a predetermined number (N in the example illustrated in FIG. 3) and a new frame is input to the frame memory 12, the imaging signal processing unit 122 deletes the oldest frame and stores a new frame in the frame memory 12. Thereafter, the processing proceeds to step S103.

(step S103) The movement amount estimation unit 21 estimates the movement amount X of a subject when the frame stored in the frame memory 12 is captured in the processing of step S101. Thereafter, the processing proceeds to step S104. The movement amount X of the subject can be estimated by comparing the frame stored in the frame memory 12 with the frame prior to the previous frame in the processing of step S102, for example, as described above. In addition, for example, the movement amount X of the subject in the first frame does not include a frame prior to the previous frame, and thus, the movement amount may not be calculated. In addition, for example, the movement amount X of the subject in the first frame does not include a frame prior to the previous frame, and thus, the movement amount may be set to zero.

(step S104) The imaging signal processing unit 122 stores the movement amount X estimated by the movement amount estimation unit 21 in the processing of step S103 in the frame memory 12 in association with the frame stored in the processing of step S102. Thereafter, the processing proceeds to step S105.

(step S105) The imaging signal processing unit 122 determines whether or not a freeze instruction is input from the CPU 123. If the imaging signal processing unit 122 determines that the freeze instruction is input, the processing proceeds to step S106 or returns to the processing of step S102 in other cases.

(step S106) The imaging signal processing unit 122 controls the image capturing driving unit 121 to stop updating the frame memory 12 of the imaging signal processing unit 122. Thereafter, the processing proceeds to step S107.

(step S107) The imaging signal processing unit 122 determines whether or not the movement amounts X of the entire frames stored in the frame memory 12 exceed a motion threshold value (predetermined threshold value). In a case where the imaging signal processing unit 122 determines that the movement amounts X of the entire frames stored in the frame memory 12 exceed the motion threshold value, the processing proceeds to step S113 or proceeds to processing of step S108 in other cases. The motion threshold value may be determined in advance or may be arbitrarily set.

(step S108) The image selection unit 13 selects a frame having the smallest movement amount X of the entire frames stored in the frame memory 12 as a reference image. Thereafter, the processing proceeds to step S109.

(step S109) The imaging signal processing unit 122 determines whether or not a gain of the reference image selected in step S108 exceeds a gain threshold value (predetermined threshold value). In a case where it is determined that the gain of the reference image exceeds the gain threshold value, the processing proceeds to step S110 or proceeds to processing of step S114 in other cases.

(step S110) The image selection unit 13 determines whether or not each frame other than the reference image stored in the frame memory 12 can be used for NR processing on a plurality of frames with respect to the reference image. In a case where there is only one frame (synthesis target image) determined to be usable for the NR processing on a plurality of frames with respect to the reference image, the processing proceeds to step S111 or proceeds to processing of step S113 in other cases. A predetermined frame (synthesis target image) may be able to be arbitrarily set.

A determination as to whether or not the frames can be used for the NR processing on a plurality of frames with respect to a reference image (determination as to whether or not the frame can be used as the synthesis target image) is made, for example, by the following method. The image selection unit 13 performs alignment of a subject in the reference image and a subject in the frame for each frame, and calculates a blurring amount of the subject in the frame with respect to the subject of the reference image. In a case where the calculated blurring amount is less than a threshold value, it is determined that the frame is a frame (synthesis target image) which can be used for the NR processing on a plurality of frames with respect to the reference image, and in a case where the calculated blurring amount is more than or equal to the threshold value, it is determined that the frame is a frame which cannot be used for the NR processing on a plurality of frames with respect to the reference image. The threshold value may be determined in advance or may be able to be arbitrarily set. In addition, any method may be used as a method of selecting the frame (synthesis target image) that can be used for the NR processing on a plurality of frames with respect to the reference image.

(step S111) The synthesis processing unit 14 synthesizes the entire frames (synthesis target image) determined to be usable for the NR processing on a plurality of frames for the reference image in the processing of step S110, with respect to the reference image selected in the processing of step S108, to generate the synthesized image. Thereafter, the processing proceeds to step S112.

(step S112) The imaging signal processing unit 122 outputs the synthesized image generated in the processing of step S111 and a freeze image determination instruction to determine the synthesized image as the freeze image to the CPU 123. Thereafter, the processing ends.

(step S113) The imaging signal processing unit 122 outputs the freeze image determination instruction to determine an image (frame) which is currently displayed in the display unit 124 as the freeze image to the CPU 123. Thereafter, the processing ends.

(step S114) The imaging signal processing unit 122 outputs the reference image selected in the processing of step S108 and the freeze image determination instruction to determine the reference image as the freeze image to the CPU 123. Thereafter, the processing ends.

Figure 7:
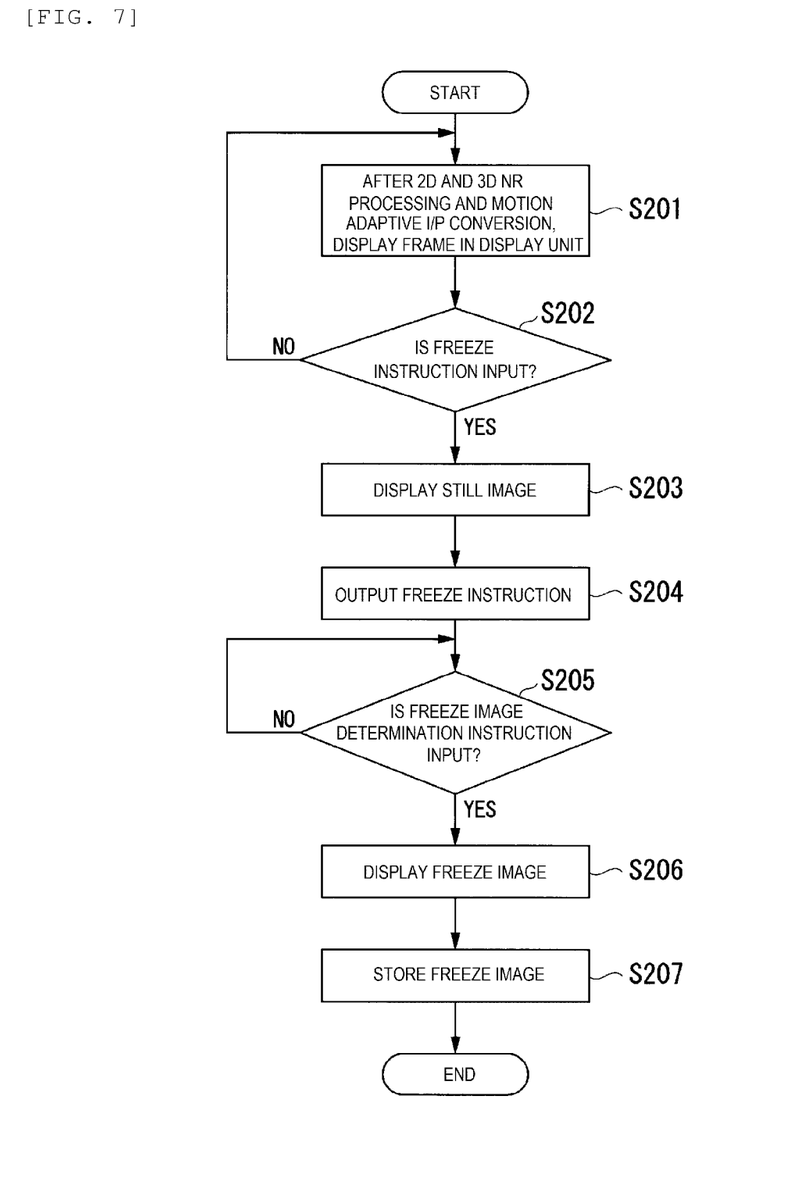
FIG. 7 is a flowchart illustrating an operation sequence of a CPU when the endoscope device starts the image capturing to generate the freeze image in the present embodiment.

FIG. 7 is a flowchart illustrating an operation sequence of the CPU 123 when the endoscope device 100 starts image capturing to generate the freeze image in the present embodiment.

(step S201) The CPU 123 performs 2D and 3D NR processing for the frame input from the imaging signal processing unit 122, and displays the frame in the display unit 124 after a motion adaptive I/P conversion. Thereafter, the processing proceeds to step S202.

(step S202) The CPU 123 determines whether or not a freeze instruction (still image acquisition instruction) is input to the input unit 128. In a case where the CPU 123 determines that the freeze instruction is input, the processing proceeds to step S203 or returns to processing of step S201 in other cases.

(step S203) The CPU 123 continuously display the frame displayed in the display unit 124 as a still image in step S201. Thereafter, the processing proceeds to step S204. (step S204) The CPU 123 outputs the freeze instruction to the imaging signal processing unit 122. Thereafter, the processing proceeds to step S205.

(step S205) The CPU 123 determines whether or not the freeze image determination instruction is input from the imaging signal processing unit 122, and in a case where the CPU 123 determines that the freeze image determination instruction is input from the imaging signal processing unit 122, the processing proceeds to step S206, otherwise the processing of step S205 is performed again.

(step S206) The CPU 123 displays the freeze image based on the freeze image determination instruction input from the imaging signal processing unit 122 in the display unit 124. Thereafter, the processing proceeds to step S207. Specifically, in a case where the freeze image determination instruction to determine the synthesized image as the freeze image is input, the CPU 123 displays the synthesized image input from the imaging signal processing unit 122 as the freeze image in the display unit 124. In addition, in a case where the freeze image determination instruction to determine the image (frame) currently displayed in the display unit 124 as the freeze image is input, the image (frame) currently displayed in the display unit 124 is displayed in the display unit 124 as the freeze image. In addition, in a case where the freeze image determination instruction to determine the reference image as the freeze image is input, the CPU 123 displays the reference image input from the imaging signal processing unit 122 in the display unit 124 as the freeze image.

(step S207) The CPU 123 stores the freeze image displayed in the display unit 124 in step S206 in the external memory unit 130. Thereafter, the processing ends.

Next, a processing sequence in which the endoscope device 100 starts image capturing and performs measurement processing will be described. In the present embodiment, the imaging signal processing unit 122 and the CPU 123 respectively perform processing, thereby, performing the measurement processing.

Figure 8:
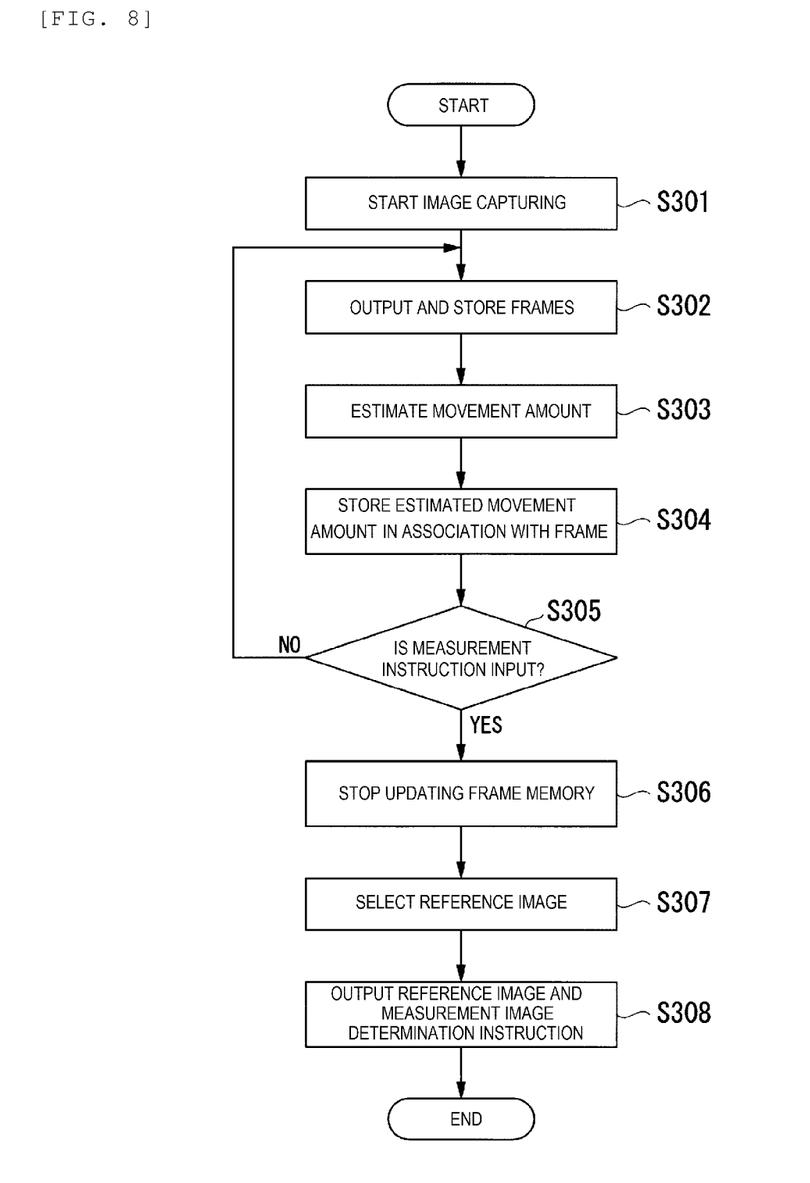
FIG. 8 is a flowchart illustrating an operation sequence of the imaging signal processing unit when the endoscope device starts the image capturing and performs measurement processing in the present embodiment.

FIG. 8 is a flowchart illustrating an operation sequence of the imaging signal processing unit 122 when the endoscope device 100 starts the image capturing and performs the measurement processing in the present embodiment. Processing of steps S301 to S304 is the same as the processing of steps S101 to S104.

(step S305) The imaging signal processing unit 122 determines whether or not a measurement instruction is input from the CPU 123. In a case where the imaging signal processing unit 122 determines that the measurement instruction is input, the processing proceeds to step S306 or returns to processing of step S302 in other cases.

(step S306) The imaging signal processing unit 122 controls the image capturing driving unit 121 to stop updating the frame memory 12 of the imaging signal processing unit 122. Thereafter, the processing proceeds to step S307.

(step S307) The image selection unit 13 selects a frame having the smallest movement amount X of the entire frames stored in the frame memory 12 as a reference image. Thereafter, the processing proceeds to step S308.

(step S308) The imaging signal processing unit 122 outputs the reference image selected in the processing of step S307 and a measurement image determination instruction to determine the reference image as a measurement image to the CPU 123. Thereafter, the processing ends.

Figure 9:
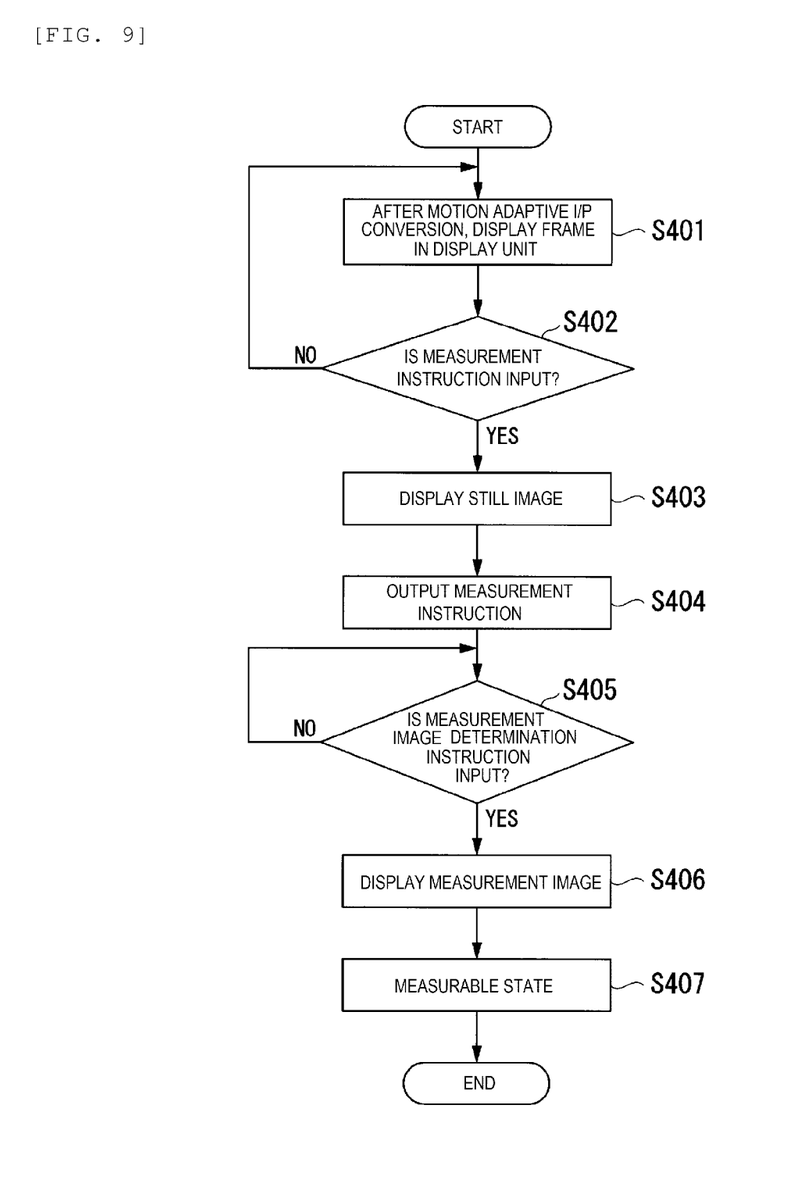
FIG. 9 is a flowchart illustrating an operation sequence of the CPU when the endoscope device starts the image capturing and performs the measurement processing in the present embodiment.

FIG. 9 is a flowchart illustrating an operation sequence of the CPU 123 when the endoscope device 100 starts image capturing and performs the measurement processing in the present embodiment.

(step S401) The CPU 123 performs a motion adaptive I/P conversion of frames input from the imaging signal processing unit 122, and thereafter displays the converted frame in the display unit 124. Thereafter, the processing proceeds to step S402.

(step S402) The CPU 123 determines whether or not a measurement instruction is input to the input unit 128. In a case where the CPU 123 determines that the measurement instruction is input, the processing proceeds to step S403 or returns to processing of step S401 in other cases.

(step S403) The CPU 123 continuously display the frame displayed in the display unit 124 as a still image in step S401. Thereafter, the processing proceeds to step S404. (step S404) The CPU 123 outputs the measurement instruction to the imaging signal processing unit 122. Thereafter, the processing proceeds to step S405.

(step S405) The CPU 123 determines whether or not the measurement image determination instruction is input from the imaging signal processing unit 122, and in a case where the CPU 123 determines that the measurement image determination instruction is input from the imaging signal processing unit 122, the processing proceeds to step S406 or the processing of step S405 is performed again in other cases.

(step S406) The CPU 123 displays a freeze image based on the measurement image determination instruction input from the imaging signal processing unit 122 in the display unit 124. Thereafter, the processing proceeds to step S407. Specifically, in a case where the measurement image determination instruction to determine the reference image as the measurement image is input, the CPU 123 displays the reference image input from the imaging signal processing unit 122 as the measurement image in the display unit 124.

(step S407) The CPU 123 sets the measurement image displayed in the display unit 124 in step S406 in a measurable state. Thereafter, the processing ends.

As described above, according to the present embodiment, when the endoscope device 100 starts image capturing to generate a freeze image, and when the movement amount X of a subject is large (when blurring is large), the CPU 123 performs 2D and 3D NR processing and sets an image obtained by performing the motion adaptive I/P conversion as the freeze image. For example, when the movement amount X of the subject is large (when the blurring is large), NR on a plurality of frames cannot be normally applied, but in the present embodiment, interlaced noise is interpolated so as not to be seen by the motion adaptive I/P conversion, not in the NR processing on a plurality of frames. Thereby, even when the movement amount X of the subject is large (when the blurring is large), it is possible to generate a freeze image with better image quality.

According to the present embodiment, when the endoscope device 100 starts image capturing to generate a freeze image, the movement amount X of a subject is small (blurring is small), and when a gain is high, a frame having the smallest movement amount X is set as a reference image and an image obtained by performing NR processing on a plurality of frames for this image is set as a freeze image. The freeze image also takes 2D NR, but does not take 3D NR as a result. In this case, the movement amount X of the subject is small (blurring is small), and since both the ODD and EVEN fields of interlace are displayed in the motion adaptive I/P conversion, the resolution is not degraded so much. In addition, random noise which increases due to a high gain is greatly reduced by effects of NR processing on a plurality of frames. Thereby, even when the movement amount X of the subject is small (blurring is small) and the gain is high, the freeze image with better image quality can be generated.

According to the present embodiment, when the endoscope device 100 starts image capturing to generate the freeze image, and when the movement amount X of the subject is small (blurring is small) and the gain is low, the frame having the smallest movement amount X is set as a reference image and the reference image is set as the freeze image. The freeze image also takes 2D NR, but does not take 3D NR as a result. Since the NR processing on a plurality of frames is averaged by overlapping a plurality of frames, there are side effects that the resolution is slightly low but the NR effects are high. Therefore, in the present embodiment, in a case where the gain is low and noises are inconspicuous although NR processing on a plurality of frames is not performed, the NR processing on a plurality of frames is not performed. Thereby, even when the movement amount X of the subject is small (blurring is small) and the gain is low, the freeze image with better image quality can be generated.

According to the present embodiment, when the endoscope device 100 starts image capturing to perform measurement processing, the NR processing on a plurality of frames or 2D/3D NR that affects measurement accuracy is not performed, and a frame with the smallest blurring among a plurality of frames stored in the frame memory 12 is selected as a measurement image to be displayed. Thereby, the measurement processing can be performed more accurately. In a case where it can be determined that the accuracy is little affected, the 2D/3D NR or the NR processing on a plurality of frames may be performed.

As described above, one embodiment of the present invention is described in detail with reference to the drawings, the specific configuration is not limited to the aforementioned embodiment, and also includes designs and the like within a range without departing from the gist of the present invention.

For example, in the operation sequence of the imaging signal processing unit 122 when the endoscope device 100 starts image capturing to generate the freeze image, in a case where the movement amount X of any frame does not exceed the motion threshold value, the reference image may be selected and the reference image may be determined as the freeze image. Thereby, a frame with a small movement amount can be determined as the freeze image, and thus, the freeze image with better image quality can be generated without performing the NR processing on a plurality of frames.

All or a part of functions of each unit included in the endoscope device 100 according to the aforementioned embodiment may also be realized by recording a program for realizing the functions in a computer-readable recording medium and by causing a computer system to read the program recorded in the recording medium. The "computer system" referred to here includes hardware such as an OS and a peripheral device.

Typically, the "computer-readable recording medium" includes a portable medium, such as a flexible disk, a magneto-optical disc, a ROM, and a CD-ROM, and a recording unit such as a hard disk embedded in a computer system, but is not limited to these. Furthermore, instead of the "computer-readable recording medium", the following means may be used. For example, a medium that dynamically holds a program may be used for a short time, like a communication line in a case where a program is transmitted via a network such as the Internet or a communication line such as a telephone line. In addition, a medium holding a program for a certain period of time may be used, like a volatile memory in a computer system serving as a server or a client in this case. In addition, the program may realize a part of the aforementioned functions, and may further realize the aforementioned functions by combining the functions with the program previously recorded in the computer system. The invention is not limited by the above description, but is limited by only the scope of appended claims.

What is claimed is:

1. An image processing device comprising:
one or more processors comprising hardware, wherein the one or more processors are configured to:
calculate an estimated movement amount of a subject in each image of a plurality of images;
perform, based on the estimated movement amounts of the plurality of images, one of:
select and output an image that is most recently captured among the plurality of images; and
select a reference image from the plurality of images based on the estimated movement amounts of the subject in the plurality of images;
in response to selecting the reference image, determine a gain of the reference image; and
perform, based on the gain of the reference image, one of:
select and output the reference image; and
a synthesis process comprising:
select a synthesis target image from the plurality of images, the synthesis target image being different from the reference image; and
generate and output a synthesized image by synthesizing the synthesis target image and the reference image,
wherein the one or more processors are configured to:
determine whether the estimated movement amounts of the plurality of images is larger than a predetermined motion value; and
in response to a determination that the estimated movement amounts of the plurality of images is larger than the predetermined motion value, select and output the image that is most recently captured among the plurality of images.

2. An image processing device comprising:
one or more processors comprising hardware, wherein the one or more processors are configured to:
calculate an estimated movement amount of a subject in each image of a plurality of images;
perform, based on the estimated movement amounts of the plurality of images, one of:
select and output an image that is most recently captured among the plurality of images; and
select a reference image from the plurality of images based on the estimated movement amounts of the subject in the plurality of images;
in response to selecting the reference image, determine a gain of the reference image; and
perform, based on the gain of the reference image, one of:
select and output the reference image; and
a synthesis process comprising:
select a synthesis target image from the plurality of images, the synthesis target image being different from the reference image; and
generate and output a synthesized image by synthesizing the synthesis target image and the reference image,
wherein the one or more processors are configured to:
determine whether the estimated movement amounts of the plurality of images is larger than a predetermined motion value; and
in response to a determination that the estimated movement amounts of the plurality of images is not larger than the predetermined motion value, select the reference image from the plurality of images based on the estimated movement amounts of the subject in the plurality of images.

3. The image processing device according to claim 2, wherein the one or more processors are configured to:
determine whether the gain of the reference image is smaller than a predetermined gain value; and
in response to a determination that the gain of the reference image is smaller than the predetermined gain value, select and output the reference image.

4. An image processing device comprising:
one or more processors comprising hardware, wherein the one or more processors are configured to:
calculate an estimated movement amount of a subject in each image of a plurality of images;
perform, based on the estimated movement amounts of the plurality of images, one of:
select and output an image that is most recently captured among the plurality of images; and
select a reference image from the plurality of images based on the estimated movement amounts of the subject in the plurality of images;
in response to selecting the reference image, determine a gain of the reference image; and
perform, based on the gain of the reference image, one of:
select and output the reference image; and
a synthesis process comprising:
select a synthesis target image from the plurality of images, the synthesis target image being different from the reference image; and
generate and output a synthesized image by synthesizing the synthesis target image and the reference image,
wherein the one or more processors are configured to:
determine whether the gain of the reference image is larger than a predetermined gain value;
in response to a determination that the gain of the reference image is larger than the predetermined gain value, determine whether there is at least one image of the plurality of images that can be selected as the synthesis target image from the plurality of images based on amounts of movements of the subject in the plurality of images relative to the reference image; and
in response to a determination that there is no image of the plurality of images that can be selected as the synthesis target image based on the amount of the amounts of movements of the subject in the plurality of images relative to the reference image, select and output the image that is most recently captured among the plurality of images.

5. An image processing device comprising:
one or more processors comprising hardware, wherein the one or more processors are configured to:
calculate an estimated movement amount of a subject in each image of a plurality of images;
perform, based on the estimated movement amounts of the plurality of images, one of:

select and output an image that is most recently captured among the plurality of images; and
select a reference image from the plurality of images based on the estimated movement amounts of the subject in the plurality of images;
in response to selecting the reference image, determine a gain of the reference image; and
perform, based on the gain of the reference image, one of:
select and output the reference image; and
a synthesis process comprising:
select a synthesis target image from the plurality of images, the synthesis target image being different from the reference image; and
generate and output a synthesized image by synthesizing the synthesis target image and the reference image,
wherein the one or more processors are configured to:
determine whether the gain of the reference image is larger than a predetermined gain value;
in response to a determination that the gain of the reference image is larger than the predetermined gain value, determine whether there is at least one image of the plurality of images that can be selected as the synthesis target image from the plurality of images based on amounts of movements of the subject in the plurality of images relative to the reference image; and
in response to a determination that there is at least one image that can be selected as the synthesis target image based on the amount of the amounts of movements of the subject in the plurality of images relative to the reference image, select the at least one image of the plurality of images as the synthesis target image.

6. An image processing device comprising:
one or more processors comprising hardware, wherein the one or more processors are configured to:
calculate an estimated movement amount of a subject in each image of a plurality of images;
perform, based on the estimated movement amounts of the plurality of images, one of:
select and output an image that is most recently captured among the plurality of images; and
select a reference image from the plurality of images based on the estimated movement amounts of the subject in the plurality of images;
in response to selecting the reference image, determine a gain of the reference image; and
perform, based on the gain of the reference image, one of:
select and output the reference image; and
a synthesis process comprising:
select a synthesis target image from the plurality of images, the synthesis target image being different from the reference image; and
generate and output a synthesized image by synthesizing the synthesis target image and the reference image,
wherein the one or more processors are configured to perform a motion adaptive interlace and progressive conversion processing on the image that is most recently captured among the plurality of images, the reference image and the synthesized image that are output.

7. A non-transitory computer-readable storage device storing instructions that cause a computer to at least:
calculate an estimated movement amount of a subject in each image of a plurality of images;
perform, based on the estimated movement amounts of the plurality of images, one of:
select and output an image that is most recently captured among the plurality of images; and
select a reference image from the plurality of images based on the estimated movement amounts of the subject in the plurality of images;
in response to selecting the reference image, determine a gain of the reference image; and
perform, based on the gain of the reference image, one of:
select and output the reference image; and
a synthesis process comprising:
select a synthesis target image from the plurality of images, the synthesis target image being different from the reference image; and
generate and output a synthesized image by synthesizing the synthesis target image and the reference image,
wherein the instructions cause the computer to:
determine whether the estimated movement amounts of the plurality of images is larger than a predetermined motion value; and
in response to a determination that the estimated movement amounts of the plurality of images is larger than the predetermined motion value, select and output the image that is most recently captured among the plurality of images.

8. A non-transitory computer-readable storage device storing instructions that cause a computer to at least:
calculate an estimated movement amount of a subject in each image of a plurality of images;
perform, based on the estimated movement amounts of the plurality of images, one of:
select and output an image that is most recently captured among the plurality of images; and
select a reference image from the plurality of images based on the estimated movement amounts of the subject in the plurality of images;
in response to selecting the reference image, determine a gain of the reference image; and
perform, based on the gain of the reference image, one of:
select and output the reference image; and
a synthesis process comprising:
select a synthesis target image from the plurality of images, the synthesis target image being different from the reference image; and
generate and output a synthesized image by synthesizing the synthesis target image and the reference image,
wherein the instructions cause the computer to:
determine whether the estimated movement amounts of the plurality of images is larger than a predetermined motion value; and
in response to a determination that the estimated movement amounts of the plurality of images is not larger than the predetermined motion value, select the reference image from the plurality of images based on the estimated movement amounts of the subject in the plurality of images.

9. The non-transitory computer-readable storage device according to claim 8, wherein the instructions cause the computer to:
determine whether the gain of the reference image is smaller than a predetermined gain value; and in response to a determination that the gain of the reference image is smaller than the predetermined gain value, select and output the reference image.

10. A non-transitory computer-readable storage device storing instructions that cause a computer to at least:
calculate an estimated movement amount of a subject in each image of a plurality of images;
perform, based on the estimated movement amounts of the plurality of images, one of:
select and output an image that is most recently captured among the plurality of images; and
select a reference image from the plurality of images based on the estimated movement amounts of the subject in the plurality of images;
in response to selecting the reference image, determine a gain of the reference image; and
perform, based on the gain of the reference image, one of:
select and output the reference image; and
a synthesis process comprising:
select a synthesis target image from the plurality of images, the synthesis target image being different from the reference image; and
generate and output a synthesized image by synthesizing the synthesis target image and the reference image,
wherein the instructions cause the computer to:
determine whether the gain of the reference image is larger than a predetermined gain value;
in response to a determination that the gain of the reference image is larger than the predetermined gain value, determine whether there is at least one image of the plurality of images that can be selected as the synthesis target image from the plurality of images based on amounts of movements of the subject in the plurality of images relative to the reference image; and
in response to a determination that there is no image of the plurality of images that can be selected as the synthesis target image based on the amount of the amounts of movements of the subject in the plurality of images relative to the reference image, select and output the image that is most recently captured among the plurality of images.

11. A non-transitory computer-readable storage device storing instructions that cause a computer to at least:
calculate an estimated movement amount of a subject in each image of a plurality of images;
perform, based on the estimated movement amounts of the plurality of images, one of:
select and output an image that is most recently captured among the plurality of images; and
select a reference image from the plurality of images based on the estimated movement amounts of the subject in the plurality of images;
in response to selecting the reference image, determine a gain of the reference image; and
perform, based on the gain of the reference image, one of:
select and output the reference image; and
a synthesis process comprising:
select a synthesis target image from the plurality of images, the synthesis target image being different from the reference image; and
generate and output a synthesized image by synthesizing the synthesis target image and the reference image,
wherein the instructions cause the computer to:
determine whether the gain of the reference image is larger than a predetermined gain value;
in response to a determination that the gain of the reference image is larger than the predetermined gain value, determine whether there is at least one image of the plurality of images that can be selected as the synthesis target image from the plurality of images based on amounts of movements of the subject in the plurality of images relative to the reference image; and
in response to a determination that there is at least one image that can be selected as the synthesis target image based on the amount of the amounts of movements of the subject in the plurality of images relative to the reference image, select the at least one image of the plurality of images as the synthesis target image.

12. A non-transitory computer-readable storage device storing instructions that cause a computer to at least:
calculate an estimated movement amount of a subject in each image of a plurality of images;
perform, based on the estimated movement amounts of the plurality of images, one of:
select and output an image that is most recently captured among the plurality of images; and
select a reference image from the plurality of images based on the estimated movement amounts of the subject in the plurality of images;
in response to selecting the reference image, determine a gain of the reference image; and
perform, based on the gain of the reference image, one of:
select and output the reference image; and
a synthesis process comprising:
select a synthesis target image from the plurality of images, the synthesis target image being different from the reference image; and
generate and output a synthesized image by synthesizing the synthesis target image and the reference image,
wherein the instructions cause the computer to perform a motion adaptive interlace and progressive conversion processing on the image that is most recently captured among the plurality of images, the reference image and the synthesized image that are output.

* * * * *